United States Patent [19]

Simone

[11] Patent Number: 5,397,786
[45] Date of Patent: Mar. 14, 1995

[54] REHYDRATION DRINK

[76] Inventor: Charles B. Simone, 123 Franklin Corner Rd., Lawrenceville, N.J. 08648

[21] Appl. No.: 3,217

[22] Filed: Jan. 8, 1993

[51] Int. Cl.$^6$ .......................... A61K 33/42; A23L 2/00
[52] U.S. Cl. .................................. 514/300; 426/74; 424/601
[58] Field of Search .................. 514/300, 11; 426/72, 426/74, 590; 424/601

[56] References Cited

U.S. PATENT DOCUMENTS

| | | | |
|---|---|---|---|
| 4,738,856 | 4/1988 | Clark | 426/74 |
| 4,871,550 | 10/1989 | Millman | 424/601 |
| 4,981,687 | 1/1991 | Fregly et al. | 424/439 |
| 5,102,871 | 4/1992 | Furukawa et al. | 514/11 |
| 5,114,723 | 5/1992 | Stray-Gundersen | 426/74 |

Primary Examiner—Arthur C. Prescott
Attorney, Agent, or Firm—Otrolenk, Faber, Gerb & Soffen

[57] ABSTRACT

A liquid composition to be used as a rehydration drink, particularly suited for the administration to people who do heavy work under severe conditions, e.g. at high temperatures, and to sportspeople and athletes, as well as to patients who exhibit dehydration symptoms due to severe illnesses such as diarrhea or vomiting, contains per serving unit water at least 1 to 100 g of at least one carbohydrate, such as glucose polymers, maltodextrin and fructose; 2 to 2500 mg of at least one electrolyte, such as an alkali and/or earth alkali salt; 0,1 to 750 mg of at least one ammonia neutralizer, such as D,L-magnesium aspartate, L-arginine and glutamate; at least one energy enhancer, such as members of the vitamin B group and branched chain amino acids; at least one antioxidant such as β-carotene, vitamin C, vitamin E and selenium; 1 to 30 mg of at least one membrane stabilizer, such as choline chloride, betaine chloride and methionine; and 1 to 200 μg of at least one neuromuscular function enhancer such as octacosanol.

19 Claims, No Drawings

REHYDRATION DRINK

BACKGROUND OF THE INVENTION

1. Field of the Invention

The present invention relates to a new liquid composition, a method for producing this composition and the use of this composition as rehydration drink.

2. Description of the Related Art

There are a number of liquid compositions or diluted mixtures on the market by the name of "Activity Drinks", "Sports Drinks" or "Nutrient Drinks" which intend to solve problems with respect to the loss of sugars, electrolytes, vitamins, minerals, amino acids, and other important nutrients due to sweating.

These drinks, however, show concentrations of electrolytes, kinds of sugars, and osmotic characteristics which are not sufficient to be totally effective in replacing the tremendous sweat losses incurred e.g. by chronically ill patients, strenuous physical activity, or the harsh conditions of tropical or desert environment. U.S. Pat. No. 4,626,527 describes a similar intent but discloses only the use of choline.

Several groups of people, including factory and farm workers and athletes can lose one to two-liters of sweat per hour with heavy clothing. Chronically ill patients or patients who rely on others to care for them may lose more fluid than what they consume. Newcomers to the desert, with clothing and heavy packs, can lose up to four liters per hour.

There are a number of serious symptoms of heat exhaustion which may develop as one loses from as little as one liter to as much as four liters or more of sweat. These symptoms include e.g. vertigo/dizziness, lightheadedness, fatigue and muscle cramps. Most of the symptoms are obvious to the individual, but sometimes lightheadedness is not, because a lightheaded individual is unable to think or act appropriately.

Thus, most of these people lose sweat which contains not only water, but more importantly, sugars, electrolytes, vitamins, minerals, amino acids, and other important nutrients. Each of these are vital for proper cellular function, including brain function.

Drinking water alone will not replace the vital nutrients and will also cause stomach cramps because of the difference of the osmotic properties of water on the one hand and stomach fluids on the other hand, and because it requires time for the body to assimilate the water.

The use of salt tablets is not recommended because the excess sodium withdraws water or suppresses more of the other vital electrolytes from the body.

OBJECT OF THE INVENTION

Since the related art did not solve the problems properly, there was a need for a proper medical formulation which will protect people and promote their well being under various adverse conditions connected with excessive loss of water, e.g. excessive perspiration.

The present invention is thus specifically concerned with the provision of a new rehydration drink. It is therefore the object of the present invention to provide a liquid composition which overcomes all the above mentioned disadvantages, and which reduces vertigo/dizziness, lightheadedness, fatigue and muscle cramps caused by excessive water loss. Fatigue as used herein means the subjective feeling of tiredness as well as the objective fatigue of muscles and the actual decrease of performance.

SUMMARY OF THE INVENTION

The solution for the objects of the invention was found in a new liquid composition comprising per serving unit:

a) 1 to 100 g of at least one carbohydrate,
b) 2 to 2500 mg of at least one electrolyte,
c) 0,1 to 750 mg of at least one ammonia neutralizer,
d) at least one energy enhancer, preferably selected from
  $d_1$) 1–2,000 µg vitamins of the vitamin B group,
  $d_2$) 10–40,000 mg L-carnitine, creatine and choline, and
  $d_3$) 1–100 mg branched-chain amino acids,
e) at least one antioxidant, preferably selected from
  $e_1$) β-carotene in a quantity of 2 µg–200 mg,
  $e_2$) vitamin C in a quantity of 10–250 mg,
  $e_3$) vitamin E in a quantity of 8–30 I.U., and
  $e_4$) selenium in a quantity of 10–300 µg,
f) 1 to 30 mg of at least one membrane stabilizer,
g) 1 to 200 µg of at least one neuromuscular enhancer, and
h) water in a quantity at least sufficient to provide a solution wherein components a) to g) are substantially dissolved and which is ready for consumption by drinking.

The ingredients of the above components a) to g) as well as the water for dissolving these ingredients (component h) should, of course, be physiologically acceptable.

The present invention also relates to a composition which is suitable for producing the above liquid composition, i.e. a solid composition containing the above components a) to g), which solid composition can be obtained by homogeneously mixing the components a) to g), and which can be converted to the above liquid composition by adding water (component h) in a quantity at least sufficient to substantially dissolve all of components a) to g) to form a drinkable solution.

DESCRIPTION OF THE PREFERRED EMBODIMENTS

Among the carbohydrates of component a) are various sugars, monosaccharides as well as oligosaccharides. Typical examples are N-acetyl-D-galactosamine, D-glucose (dextrose, grape sugar, corn sugar), D-glucosamine, N-acetyl-D-glucosamine, N-methyl-D-glucosamine, D-mannose, D-ribose, D-xylose D-fructose, D-galactose, D-galactosamine, cellobiose, maltose, galactose, and sucrose.

These carbohydrates are either in the form of monomers like D-fructose or in the form of polymers e.g. glucose polymers, such as maltose or maltodextrin, in which a series of glucose molecules is bond together chemically. Such polymers can be made from any of the above sugars, which are cleaved enzymatically in the body; this process consequently provides a constant source of energy made available to the body over a course of one to two hours.

The preferred carbohydrates are the glucose polymers, maltodextrin and fructose in crystalline pure form; most preferred are the glucose polymers. The preferred range of the carbohydrates is 1 to 35 mg.

The component b) is an electrolyte, particularly mineral salt. Preferred electrolytes are salts of a metal of the group I and II of the Periodic System, preferably the inorganic and organic salts of sodium, potassium, calcium and/or magnesium. Examples of such salts are sodium acetate, acidic sodium citrate, acidic sodium phosphate, sodium amino salicylate, sodium bicarbonate, sodium bromide, sodium chloride, sodium citrate, sodium lactate, sodium phosphate, sodium salicylate, sodium sulphate (anhydrous), sodium sulphate (Glauber's salt), potassium acetate, potassium bicarbonate, potassium bromide, potassium chloride, potassium citrate, potassium-D-gluconate, mono- and dibasic potassium phosphate, calcium acetate, calcium chloride, calcium citrate, calcium-D-gluconate, calcium lactate, calcium laevulinate, dibasic calcium phosphate, magnesium chloride and magnesium sulphate.

The preferred salts are sodium bicarbonate, sodium phosphate, potassium bicarbonate, potassium chloride, dibasic potassium phosphate, calcium carbonate and magnesium carbonate. The electrolytes are present in amounts of 2 to 2500 mg, preferably in amounts of 5 to 1,000 mg.

Ammonia neutralizers of component c) are mainly amino acids e.g. $\alpha$-alanine, arginine, asparagine, cystine, cysteine, aspartic acid, glutamic acid, glutamine, glycine, histidine, $\delta$-hydroxylysine, hydroxyproline, lysine, 3-monoiodotyrosine, leucine, methionine, norleucine, phenylalanine, proline, threonine, serine, tyrosine, tryptophan and the salts thereof, e.g. the potassium, magnesium and the phosphate salts.

Preferred amino acids or salts thereof are D,L-magnesium aspartate, L-arginine and glutamate. The preferred range of the amino acids is 5 to 250 mg.

Energy enhancers of component d) are preferably vitamins of the vitamin B group, e.g. vitamin B1 (thiamin, aneurin), vitamin B2 (riboflavin), vitamin PP (niacinamide), vitamin B6 (pyridoxine), pantothenic acid and L-carnitine; creatine, choline (chloride or its other forms); and branched chain amino acids, particularly leucine, valine and isoleucine. Preferred quantities of vitamins of the B group (component $d_1$) are 10–500 $\mu$g, preferred quantities of L-carnitine, creatine and choline (component $d_2$) are 50–500 mg and preferred quantities of branched-chain amino acids (leucine, isoleucine and valine) are 3–10 mg.

Preferred quantities of antioxidants (component e) are as follows: $\beta$-carotene: 5–100 $\mu$g, vitamin C: 20–100 mg, vitamin E: 10–20 I.U., and selenium: 50–200 $\mu$g. Membrane stabilizers of component f) are preferably betain and methionine in a range of 1–30 mg, preferably 4 to 10 mg.

An example of a neuromuscular enhancer (component g) is the choline (choline chloride) already referred to under d) above. Preferred neuromuscular enhancers are higher saturated fatty alcohols, particularly $C_{25}$–$C_{30}$ fatty alcohols, preferably octacosanol (cerotyl alcohol) which can be used in quantities of 1–2,000 $\mu$g, preferably 3–20 $\mu$g, most preferably about 5 $\mu$g.

Within the broad scope of the invention described above, two lines of more specific compositions have been developed, which constitute preferred embodiments of the invention. The first line embraces compositions which are particularly suited for the administration to people who do heavy work under severe conditions and particularly at high ambient temperatures and to sports enthusiasts and athletes. This line is represented by the compositions under the heading "Drink A" in Table 1 below. The second line embraces compositions which are particularly suited for patients who exhibit dehydration symptoms due to severe diarrhea or vomiting for a variety of causes such as gastrointestinal disorders, cardiovascular disorders, and chronic illnesses, such as cancer. Compositions of this type are represented by those set forth under the heading "Drink B" in Table 1 below. Figures underlined in Table 1 (such as "32" relating to "Glucose Polymers" in the left column) refer to the specific "Drink A" and "Drink B" respectively, administered in the course of the tests which will be described later-on. The compositions containing these underlined quantities of ingredients are particularly preferred.

The quantities of the various components of the compositions according to the present invention relate, throughout the specification and the claims, in each case to serving units or rations, i.e. to quantities of drink served, administered or consumed at one time. It will be well understood that such serving units are commonly not prepared individually. For the sake of simplicity and economy greater quantities are usually prepared which are composed of multiples of such serving units. Accordingly, it must be kept in mind that the figures relating to these serving units must be extrapolated by multiplication by any desired multiplicator so that any desired quantity of a composition is included. Thus, although the figures shown in Table 1 and elsewhere in the specification as well as in the claims relate to a serving unit, they have to be understood as comprising any multiple thereof.

In preparing the various liquid compositions, the components listed in Table 1 are homogeneously mixed and dissolved in a sufficient quantity of water to provide a solution ready for consumption by drinking.

TABLE 1

| Ingredients | Drink A | Drink B |
|---|---|---|
| CARBOHYDRATES | | |
| Glucose Polymers (g) | 20-26-32-50-100 | 7-10-14-40-80 |
| Maltodextrin (mg) | 10-20-30-50-15 | 10-15-25-50-100 |
| Fructose (g) | 1-1.5-2-5-15 | 1-1.5-2-5-15 |
| ELECTROLYTES | | |
| $KHCO_3$ (mg) | 100-500-960-1500-2500 | 50-100-200-500-1500 |
| $NaHCO_3$ (mg) | 20-30-40-5-60 | 2-3-4-5-10 |
| KCl (mg) | 100-150-200-500-2,000 | 20-30-40-800-1500 |
| $K_3PO_4$ (mg) | 100-150-200-500-2,000 | 20-30-40 40-800-1500 |
| $Na_3PO_4$ (mg) | 50-150-300-500-750 | 5-15-30-50-75 |
| $CaCO_3$ (mg) | 5-15-20-40-200 | 5-15-20-40-200 |
| $MgCO_3$ (mg) | 5-15-20-40-200 | 5-15-20-40-200 |
| AMMONIA NEUTRALIZERS | | |
| D,L-Aspartic Acid or Magnesium Aspartate (mg) | 10-100-200-500-750 | 1-10-20-50-75 |
| L-Arginine ($\mu$g) | 20-100-200-500-750 | 2-10-20-50-75 |

TABLE 1-continued

| Ingredients | Drink A | Drink B |
|---|---|---|
| Glutamate (mg) | 1-5-10-30-100 | 1-5-10-30-50 |
| ENERGY ENHANCERS | | |
| Vitamin B1 ($\mu$g) | 1-3-5-50-500 | 1-3-5-50-500 |
| vitamin B2 ($\mu$g) | 10-50-100-500-2,000 | 10-50-100-500-2000 |
| Niacinamide ($\mu$g) | 10-50-100-500-2,000 | 10-50-100-500-2000 |
| Vitamin B6 ($\mu$g) | 10-50-100-500-2,000 | 10-50-100-500-2000 |
| Pantothenic Acid ($\mu$g) | 10-50-100-500-2,000 | 10-50-100-500-2000 |
| L-Carnitine (mg) | 10-50-100-500-2,000 | 1-50-10-50-200 |
| Creatine (mg) | 10-50-100-500-1,000 | 5-8-10-50-200 |
| Choline chloride (mg) | 4-200-400-4000-40,000 | 4-20-40-400-4,000 |
| BRANCHED CHAIN AMINO ACIDS | | |
| Leucine (mg) | 1-3-5-10-50 | 1-3-5-10-50 |
| Isoleucine (mg) | 1-3-5-10-100 | 1-3-5-10-100 |
| Valine (mg) | 1-3-5-10-100 | 1-3-5-10-100 |
| ANTIOXIDANTS | | |
| Beta-Carotene ($\mu$g) | 5-8- 10-100-200 | 2-3-5-10-100 |
| Vitamin C (mg) | 20-30-60-120-250 | 10-30-60-70-90 |
| Vitamin E (I.U.) | 10-12-15-20-30 | 8-9-10-12-15 |
| Selenium ($\mu$g) | 10-50-100-200-300 | 10-20-50-100-200 |
| MEMBRANE STABILIZERS or METHYLDONORS | | |
| Betaine chloride ($\mu$g) | 1-3-5-10-25 | 1-3-5-10-25 |
| Methionine ($\mu$g) | 3-4-5-20-30 | 1-3-5-10-20 |
| NEUROMUSCULAR ENHANCERS | | |
| Octacosanol ($\mu$g) | 1-3-5-100-200 | 1-3-5-10-20 |

The preferred liquid composition of the present invention combines about 30 different macronutrients and micronutrients. Very surprisingly, a truly spectacular result is obtained, eliminating nearly completely all fatigue and dehydration symptoms, in both the sports and with dehydrated patients.

The new liquid composition according to the present invention can be manufactured by known methods, e.g. powdering each compound a) through g), mixing them together in the ranges of the amounts given, diluting the resulting mixture with water, and homogenising.

In view of the specific qualitative and quantitative combination of the components a) through g), the liquid composition is useful as rehydration drink. This drink replaces the nutrients and water losses which occur while sweating during physical exertion or water losses due to diarrhea or vomiting. This drink can be administered to a human body with no restriction concerning age, sex, medical history, drug therapy and food consumption, who lost water and nutrients in different ways and for different reasons, especially patients who e.g. clinically exhibit dehydration symptoms, sports enthusiasts and people who require sustained energy. The drink is also useful for patients in nursing homes and hospitals, patients with diarrhea, people who work outdoors, professional athletes, or those who require sustained energy while working. Finally the drink is effective under tropical or desert conditions to compensate for the quantity of liquid lost. The drink may be given a pleasant taste to stimulate consumption.

The following tests were carried out using compositions according to the present invention (Drink A and Drink B):

Two groups of people (group I and II) were analysed. Group I was composed of 25 people who were active athletes involved in many sports, particularly basketball, soccer and American football. Group II was composed of 20 patients who clinically exhibited dehydration symptoms secondary to severe diarrhea or vomiting from a variety of causes including cancer, gastrointestinal disorders, and chronically institutionalized patients.

"Quality of life scales", a term which is used for describing a series of qualities of life, are an acceptable way of evaluating any treatment not by the physician, but rather by the patient himself/herself. The patient decides whether the treatment is beneficial or not. These scales have been successfully used to evaluate cardiovascular treatments, cancer treatments, and treatments of other chronic illnesses.

The scoring system is simple. The person decides if the treatment has improved, worsened, or has made no change in his/her life during the treatment period. Each person is asked to score themselves before and after using the drink. The amount served was 1 cup (1 serving unit) of Drink A containing about 33 g of carbohydrates and about 132 calories, and 1 cup (1 serving unit) of Drink B containing about 15 g of carbohydrates and about 60 calories. Either drink would have been all right for either group, but athletes need more energy and drink A has more energy calories as well as enhancing agents. The results of these tests are shown in Table 2.

TABLE 2

| | Quality of Life Scales | | | | | |
|---|---|---|---|---|---|---|
| | Group I/Drink A | | | Group II/Drink B | | |
| | Improve | No Change | Worsen | Improve | No Change | Worsen |
| Physical Symptoms | 25 | | | 19 | 1 | |
| Fatigue | | | | | | |
| Dizziness, Vertigo | | | | | | |
| Lightheadedness | | | | | | |
| Muscle cramps | | | | | | |

TABLE 2-continued

| | Quality of Life Scales | | | | | |
|---|---|---|---|---|---|---|
| | Group I/Drink A | | | Group II/Drink B | | |
| | Improve | No Change | Worsen | Improve | No Change | Worsen |
| Performance | 23 | 2 | | 18 | 2 | |
| General Well Being | 25 | | | 20 | | |
| Cognitive Abilities | 25 | | | 17 | 3 | |
| Life Satisfaction | 25 | | | 20 | | |

Further tests were made with Group I and Group II people and with Drink A and Drink B. Blood values were obtained of all 25 patients in Group I (athletes) and all 20 patients in Group II (patients) before and after administration of the rehydration drink A to Group I and Drink B to Group II.

Group I- Active Athletes:

A blood sample was obtained on all athletes half way through the end of the strenuous exercise. For example, this was at half time of the basketball, soccer, or American football game, or half way through (at least 45 minutes) a strenuous exercise work-out for others (body-builders, runners, etc.). After the blood was obtained, the athletes began to drink four to six oz. of Drink A every 15 to 20 minutes until the games or exercises were completed, at which time a second blood sample was obtained. The two sets of blood values were compared (Tables 3 to 6).

The first blood samples were analysed and consistently revealed a picture of Type A Lactic Acidosis due to hypoxemia in this group. Lactic acidosis is characterized by:

1) Increased Anion Gap (A. G.) ( >25 mEq/l; normal range=8–16 mEq/1). The Anion Gap is defined as: Sodium (Na)-[Chloride (Cl)+Bicarbonate $(HCO_3)$]

2) Decreased serum bicarbonate ( normal range 24–26 mEq/l)
3) Increased serum potassium (>5.5; normal 3,5–5,3 mEq/l)
4) Low or normal serum chloride (normal 96–109 mEq/l)
5) Increased serum uric acid (normal range=3–9 mg/dl)
6) Increased serum phosphorus (normal range 2,5–4,5 mg/dl)
7) Increased serum SGOT (normal range 0–40 Units/liter)
8) Increased serum LDH (normal range 100–225 Units/liter)
9) Decreased urine pH (normal range 5.1–9.0)
10) Increased lactate (>5, normal range 0–1.6 mEq/liter)

TABLE 3

Blood Values (a. normal range, and of Athletes No. 1 through 25 at half-time of exercise, before rehydration drink A was administered:

| No a. | Na 135–147 | Cl 96–109 | HCO3 24–26 | A.G. 8–16 | Lact 0–16 | K 3.5–5.3 | Uric Acid 3–9 | P 2.5–4.5 | Urin pH 5.2–9.0 | SGOT 0–40 | LDH 100–225 |
|---|---|---|---|---|---|---|---|---|---|---|---|
| 1 | 140 | 93 | 20 | 27 | 6.1 | 5.8 | 11 | 4.7 | 5.0 | 41 | 230 |
| 2 | 146 | 96 | 23 | 27 | 7.1 | 5.6 | 12 | 4.9 | 4.0 | 42 | 227 |
| 3 | 147 | 100 | 22 | 25 | 5.5 | 5.7 | 9 | 5.1 | 5.0 | 40 | 232 |
| 4 | 141 | 95 | 22 | 24 | 5.1 | 5.9 | 10 | 4.6 | 5.0 | 35 | 234 |
| 5 | 137 | 95 | 20 | 22 | 5.2 | 5.7 | 8 | 4.8 | 5.0 | 42 | 224 |
| 6 | 138 | 93 | 22 | 23 | 5.6 | 6.1 | 11 | 5.0 | 5.0 | 45 | 226 |
| 7 | 142 | 95 | 21 | 26 | 5.9 | 6.0 | 13 | 4.7 | 5.0 | 39 | 229 |
| 8 | 145 | 94 | 20 | 31 | 6.8 | 5.7 | 15 | 4.8 | 4.0 | 44 | 246 |
| 9 | 144 | 95 | 21 | 28 | 6.3 | 6.0 | 14 | 4.6 | 4.0 | 43 | 241 |
| 10 | 142 | 93 | 21 | 28 | 6.2 | 5.6 | 15 | 4.5 | 4.0 | 42 | 229 |
| 11 | 139 | 92 | 20 | 27 | 6.2 | 6.1 | 13 | 4.7 | 4.0 | 44 | 225 |
| 12 | 146 | 94 | 23 | 29 | 6.3 | 5.8 | 16 | 4.8 | 4.0 | 42 | 232 |
| 13 | 145 | 95 | 21 | 29 | 6.6 | 5.9 | 14 | 5.0 | 4.0 | 41 | 234 |
| 14 | 144 | 93 | 22 | 29 | 6.6 | 5.7 | 13 | 4.9 | 4.0 | 47 | 227 |
| 15 | 146 | 94 | 21 | 31 | 7.1 | 6.2 | 17 | 5.0 | 4.0 | 45 | 239 |
| 16 | 139 | 94 | 21 | 24 | 5.6 | 5.6 | 11 | 4.6 | 5.0 | 41 | 235 |
| 17 | 135 | 93 | 22 | 30 | 7.0 | 6.1 | 16 | 4.9 | 4.0 | 46 | 239 |
| 18 | 143 | 94 | 21 | 28 | 6.4 | 6.0 | 12 | 5.0 | 4.0 | 42 | 241 |
| 19 | 142 | 95 | 22 | 25 | 5.9 | 5.7 | 9 | 4.6 | 5.0 | 36 | 235 |
| 20 | 145 | 94 | 20 | 31 | 6.8 | 6.3 | 13 | 4.9 | 4.0 | 47 | 236 |
| 21 | 139 | 92 | 20 | 27 | 5.9 | 6.1 | 15 | 4.9 | 5.0 | 44 | 228 |
| 22 | 140 | 94 | 21 | 25 | 5.4 | 5.6 | 9 | 5.0 | 4.0 | 42 | 226 |
| 23 | 146 | 93 | 23 | 30 | 6.8 | 6.1 | 16 | 5.1 | 4.0 | 46 | 234 |
| 24 | 143 | 92 | 20 | 31 | 6.7 | 6.3 | 14 | 4.8 | 4.0 | 45 | 237 |
| 25 | 147 | 97 | 22 | 28 | 6.6 | 5.9 | 13 | 4.7 | 4.0 | 41 | 231 |

TABLE 4

Hallmarks of lactic acidosis seen in athletes, especially type A which is due to hypoxemia, the number of athletes with those values and the range.

| blood parameter | hallmark of lactic acidosis | number of athletes with normal value | range of athletes blood values |
|---|---|---|---|
| anion gap (A.G.) | >25 mEq/lt | 23 of 25 | 22–31 |
| lactate level | >5.0 mEq/lt | All 25 | 5.1–7.1 |
| urine pH | <5.2 | All 25 | 4.0–5.0 |

TABLE 4-continued

Hallmarks of lactic acidosis seen in athletes, especially type A which is due to hypoxemia, the number of athletes with those values and the range.

| blood parameter | hallmark of lactic acidosis | number of athletes with normal value | range of athletes blood values |
|---|---|---|---|
| chloride level | low or <96 mEq/lt | 23 of 25 | 92–100 |
| bicarbonate level | <24 mEq/lt | All 25 | 20–23 |
| potassium level | >5.6 mEq/lt | All 25 | 5.6–6.3 |
| uric acid level | >9 mg/dl | 24 of 25 | 8–17 |
| phosphorus | >4.5 mg/dl | All 25 | 4.5–5.1 |
| SGOT | >40 IU/l | 22 of 25 | 35–47 |
| LDH | >225 IU/l | 24 of 25 | 225–246 |

TABLE 5

Blood Values of group I athletes at the end of game/exercise after administration of rehydration drink A

| No a. | Na 135–147 | Cl 96–109 | HCO3 24–26 | A.G. 8–16 | K Lact 0–16 | Uric 3.5–5.3 | P Acid 3–9 | pH 2.5–4.5 | Urin 5.2–9.0 | SGOT 0–40 | LDH 100–225 |
|---|---|---|---|---|---|---|---|---|---|---|---|
| 1 | 140 | 105 | 25 | 10 | 0.8 | 3.9 | 8.0 | 4.1 | 8.0 | 31 | 109 |
| 2 | 142 | 106 | 24 | 12 | 1.2 | 5.0 | 7.0 | 4.0 | 8.0 | 27 | 201 |
| 3 | 139 | 103 | 26 | 10 | 1.1 | 4.9 | 7.0 | 3.7 | 6.0 | 36 | 217 |
| 4 | 141 | 101 | 25 | 15 | 1.5 | 5.1 | 8.0 | 2.9 | 8.0 | 26 | 222 |
| 5 | 147 | 108 | 26 | 13 | 0.5 | 3.8 | 3.0 | 3.1 | 8.0 | 29 | 199 |
| 6 | 137 | 99 | 26 | 12 | 1.4 | 4.7 | 5.0 | 3.9 | 7.0 | 40 | 109 |
| 7 | 140 | 108 | 24 | 8 | 1.1 | 4.5 | 8.0 | 4.3 | 6.0 | 19 | 216 |
| 8 | 136 | 101 | 25 | 10 | 1.2 | 3.9 | 4.0 | 3.0 | 7.0 | 26 | 193 |
| 9 | 139 | 99 | 26 | 14 | 1.5 | 4.2 | 7.0 | 2.7 | 9.0 | 37 | 129 |
| 10 | 142 | 105 | 24 | 13 | 0.9 | 4.8 | 5.0 | 3.6 | 8.0 | 24 | 147 |
| 11 | 137 | 96 | 25 | 16 | 1.3 | 4.1 | 3.0 | 3.3 | 8.0 | 19 | 192 |
| 12 | 145 | 107 | 26 | 12 | 0.2 | 3.7 | 5.0 | 4.2 | 6.0 | 26 | 178 |
| 13 | 140 | 99 | 26 | 15 | 1.4 | 5.0 | 4.0 | 2.8 | 7.0 | 30 | 201 |
| 14 | 147 | 108 | 25 | 14 | 0.7 | 4.3 | 8.0 | 4.1 | 8.0 | 27 | 219 |
| 15 | 137 | 96 | 25 | 16 | 0.3 | 4.0 | 6.0 | 3.6 | 6.0 | 161 | 184 |
| 16 | 135 | 97 | 24 | 14 | 1.2 | 5.0 | 4.0 | 2.5 | 6.0 | 32 | 191 |
| 17 | 139 | 99 | 24 | 16 | 0.9 | 5.2 | 7.0 | 2.7 | 8.0 | 22 | 217 |
| 18 | 140 | 105 | 25 | 10 | 0.6 | 3.7 | 4.0 | 3.7 | 7.0 | 12 | 157 |
| 19 | 145 | 108 | 24 | 13 | 0.4 | 5.1 | 8.0 | 4.0 | 6.0 | 25 | 152 |
| 20 | 138 | 103 | 26 | 9 | 1.4 | 3.9 | 3.0 | 3.2 | 8.0 | 8 | 183 |
| 21 | 142 | 106 | 25 | 11 | 0.8 | 4.7 | 4.0 | 2.9 | 6.0 | 36 | 222 |
| 22 | 143 | 107 | 24 | 12 | 1.3 | 4.4 | 7.0 | 2.7 | 7.0 | 25 | 166 |
| 23 | 137 | 102 | 24 | 11 | 0.6 | 3.6 | 5.0 | 4.5 | 6.0 | 30 | 200 |
| 24 | 140 | 99 | 26 | 15 | 1.3 | 4.8 | 7.0 | 3.9 | 8.0 | 17 | 226 |
| 25 | 145 | 104 | 25 | 16 | 0.7 | 5.1 | 8.0 | 3.1 | 6.0 | 39 | 196 |

TABLE 6 shows that all 25 athletes had normal blood values after drinking rehydration drink A:

| blood parameter | hallmark of lactic acidosis | number of athletes with this value | range of athletes' blood values |
|---|---|---|---|
| anion gap | >25 mEq/lt | all 25 | 8–16 |
| lactate level | >5.0 mEq/lt | all 25 | 0.2–1.5 |
| urine pH | <5.2 | all 25 | 6–9 |
| chloride level | low or <96 mEq/lt | all 25 | 96–108 |
| bicarbonate level | <24 mEq/lt | all 25 | 24–26 |
| potassium level | >5.6 mEq/lt | all 25 | 3.6–5.2 |
| uric acid level | >9 mg/dl | all 25 | 3–8 |
| phosphorus | >4.5 mg/dl | all 25 | 2.5–4.5 |
| SGOT | >40 IU/l | all 25 | 8–40 |
| LDH | >225 IU/l | all 25 | 109–226 |

Group II - Patients

A blood sample was obtained of all 20 patients with various illnesses listed in Table 7. After drinking four to six ounces of the rehydration drink B every 20 to 30 minutes for two and a half to three hours, a second blood specimen was obtained. The two sets of blood values were compared.

Three patients had diarrhea which produces a metabolic acidosis characterized by low bicarbonate, a normal to low chloride, and unlike lactic acidosis, a low potassium, and a low sodium. These features are shown in Table 7.

Two patients had nausea and vomiting which produces a metabolic alkalosis characterized by an elevated bicarbonate, an elevated sodium, a low potassium, and a normal to low chloride. Both patients had these blood changes. Lactic acidosis Type B (no clinical tissue hypoxia) seen with Infections, Diabetes, Cancer, and Alcohol use; Lactic acidosis Type A (due to clinically apparent hypoxia) seen with dehydration in nursing home patients.

TABLE 7

Blood Values (a.: normal. and of 20 Group II patients before the administration of rehydration drink B (Diar = diarrhoea; Naus = nausea, vomiting; Alc = Alcohol; Inf = infections; Diab = diabetes; Canc = cancer; Home = dehydrated nurse home patients)

| No a. | Na 135–147 | Cl 96–109 | HCO3 24–26 | A.G. 8–16 | K Lact 0–16 | Uric 3.5–5.3 | P Acid 3–9 | pH 2.5–4.5 | Urin 5.2–9.0 | LDH SGOT 0–40 | 100–225 |
|---|---|---|---|---|---|---|---|---|---|---|---|
| Diar | 129 | 95 | 17 | 17 | 5.2 | 3.3 | 18.0 | 4.9 | 4 | 46 | 236 |
| Diar | 130 | 96 | 15 | 19 | 4.9 | 3.4 | 17 | 5.1 | 4 | 41 | 241 |
| Diar | 127 | 94 | 15 | 18 | 5.3 | 3.1 | 15.0 | 4.7 | 5 | 48 | 229 |
| Naus | 150 | 94 | 28 | 28 | 0.8 | 3.2 | 16.0 | 4.6 | 9 | 40 | 226 |
| Naus | 151 | 93 | 30 | 28 | 1.1 | 3.0 | 18.0 | 4.7 | 9 | 47 | 230 |
| Inf | 141 | 93 | 23 | 25 | 2.4 | 5.8 | 12 | 5.1 | 3 | 40 | 240 |
| Inf | 143 | 94 | 21 | 28 | 2.7 | 6.2 | 13 | 4.9 | 4 | 46 | 237 |
| Diab | 146 | 99 | 20 | 27 | 5.1 | 5.6 | 11 | 5.2 | 4 | 40 | 245 |
| Diab | 144 | 95 | 21 | 28 | 5.2 | 5.9 | 19 | 5.0 | 3 | 44 | 235 |
| Diab | 139 | 93 | 20 | 26 | 5.7 | 5.7 | 12 | 4.8 | 3 | 42 | 228 |
| Canc | 140 | 91 | 21 | 28 | 5.9 | 5.8 | 15 | 5.3 | 4 | 53 | 317 |
| Canc | 142 | 95 | 22 | 25 | 6.2 | 5.9 | 17 | 4.9 | 5 | 49 | 300 |
| Canc | 137 | 92 | 22 | 23 | 5.6 | 6.1 | 13 | 4.6 | 3 | 52 | 278 |
| Canc | 138 | 94 | 21 | 23 | 6.0 | 6.2 | 16 | 5.1 | 4 | 61 | 259 |
| Alc | 147 | 101 | 21 | 25 | 5.0 | 5.9 | 14 | 4.9 | 4 | 59 | 266 |
| Home | 145 | 93 | 22 | 30 | 7.0 | 6.1 | 16 | 4.9 | 4 | 46 | 242 |
| Home | 139 | 92 | 20 | 27 | 6.2 | 6.1 | 13 | 4.7 | 4 | 49 | 225 |
| Home | 143 | 92 | 20 | 31 | 6.5 | 6.0 | 14 | 4.9 | 5 | 47 | 236 |
| Home | 142 | 95 | 22 | 25 | 7.0 | 5.6 | 16 | 5.1 | 3 | 36 | 226 |
| Home | 136 | 92 | 21 | 23 | 4.6 | 6.0 | 12 | 4.8 | 4 | 45 | 233 |

All 20 patients demonstrate the characteristic blood changes seen with the disorders listed, whether it be metabolic acidosis associated with diabetes, metabolic alkalosis associated with nausea and vomiting, or lactic acidosis associated with infections, diabetes, cancer, alcohol, or dehydration seen in nursing home patients who are not well attended and who forget to drink on a regular basis.1

Each blood parameter became normal for all patients studied after the rehydration drink B was given to them as shown in:

TABLE 8

Blood Values (a.: normal, and of 20 Group II patients after the administration of rehydration drink B (Diar = diarrhoea; Naus = nausea, vomiting; Alc = Alcohol; Inf = infections; Diab = diabetes; Canc = cancer; Home = dehydrated nurse home patients)

| No a. | Na 135–147 | Cl 96–109 | HCO3 24–26 | A.G. 8–16 | K Lact 0–16 | Uric 3.5–5.3 | P Acid 3–9 | pH 2.5–4.5 | Urin 5.2–9.0 | LDH SGOT 0–40 | 100–225 |
|---|---|---|---|---|---|---|---|---|---|---|---|
| Diar | 141 | 99 | 26 | 16 | 0.9 | 5.1 | 8 | 4.2 | 8 | 40 | 148 |
| Diar | 139 | 103 | 24 | 12 | 1.3 | 4.9 | 3 | 2.9 | 6 | 22 | 217 |
| Diar | 143 | 105 | 25 | 13 | 1.0 | 4.6 | 6 | 3.6 | 9 | 31 | 196 |
| Naus | 140 | 107 | 24 | 9 | 0.8 | 5.2 | 9 | 4.1 | 5 | 19 | 154 |
| Naus | 145 | 108 | 26 | 11 | 1.4 | 5.0 | 5 | 2.6 | 6 | 27 | 219 |
| Inf | 142 | 104 | 24 | 14 | 0.7 | 3.7 | 7 | 4.0 | 7 | 12 | 201 |
| Inf | 136 | 102 | 25 | 9 | 0.4 | 4.9 | 4 | 2.8 | 8 | 25 | 224 |
| Diab | 144 | 106 | 26 | 12 | 1.5 | 5.4 | 8 | 3.5 | 6 | 36 | 133 |
| Diab | 135 | 101 | 25 | 9 | 1.2 | 4.7 | 9 | 4.4 | 7 | 33 | 168 |
| Diab | 146 | 109 | 24 | 13 | 1.4 | 5.2 | 3 | 2.9 | 9 | 34 | 214 |
| Canc | 137 | 98 | 25 | 14 | 0.9 | 4.0 | 4 | 3.3 | 7 | 55 | 309 |
| Canc | 139 | 97 | 26 | 16 | 1.1 | 4.7 | 8 | 4.3 | 6 | 47 | 294 |
| Canc | 142 | 105 | 24 | 13 | 0.8 | 5.0 | 5 | 3.9 | 8 | 60 | 281 |
| Canc | 147 | 108 | 26 | 13 | 1.6 | 5.3 | 7 | 4.5 | 6 | 59 | 262 |
| Alc | 138 | 99 | 25 | 14 | 1.5 | 4.2 | 7 | 2.7 | 9 | 38 | 199 |
| Home | 140 | 107 | 24 | 9 | 1.3 | 3.9 | 3 | 4.2 | 8 | 19 | 209 |
| Home | 145 | 109 | 26 | 10 | 0.8 | 3.6 | 4 | 3.0 | 6 | 20 | 200 |
| Home | 139 | 100 | 24 | 15 | 1.5 | 5.1 | 6 | 3.7 | 7 | 40 | 155 |
| Home | 141 | 103 | 25 | 13 | 1.1 | 4.5 | 9 | 2.6 | 6 | 35 | 205 |
| Home | 143 | 106 | 24 | 13 | 1.0 | 3.7 | 8 | 4.4 | 9 | 15 | 186 |

CONCLUSION: For both groups of athletes (Group I) and patients (Group II) it was demonstrated that their initial blood values were consistent with the acid-base disorder characteristic for those specific groups. It was further demonstrated that the blood abnormalities became normalized after each person drank rehydration drink A or B respectively.

I claim:

1. A liquid composition to be used as a rehydration drink, containing per serving unit at least the following components:

a) 1 to 100 g of at least one carbohydrate,
b) 2 to 2500 mg of at least one electrolyte,
c) 0.1 to 750 mg of at least one ammonia neutralizer,
d) at least one energy enhancer,
e) at least one antioxidant, g) 1 to 200 μg of at least one neuromuscular function enhancer selected from the group consisting of choline and a higher saturated fatty alcohol, and h) water in a quantity at least sufficient for provide a solution wherein components a) to g) are substantially dissolved and which solution is ready for consumption by drinking.

2. A composition according to claim 1, wherein the carbohydrate is selected from the group consisting of monosaccharides, oligosaccharides, glucose polymers, maltodextrin and fructose.

3. A composition according to claim 1, wherein the electrolyte is selected from the group consisting of salts of a metal of Group I and II of the periodic system.

4. A composition according to claim 3, wherein the electrolyte is selected from the group consisting of sodium bicarbonate, sodium phosphate, acidic sodium phosphate, potassium bicarbonate, potassium chloride, dibasic potassium phosphate, calcium carbonate and magnesium carbonate.

5. A composition according to claim 1, wherein the ammonia neutralizer is selected from the group consisting of amino acids and their salts.

6. A composition according to claim 5, wherein the ammonia neutralizer is selected from the group consisting of D,L-magnesium aspartate, L-arginine and glutamate.

7. A composition according to claim 1, wherein the energy enhancer is selected from the group consisting of vitamins of vitamin B group and branched chain amino acids.

8. A Composition according to claim 7, wherein the energy enhancer is selected from the group consisting of vitamins of the vitamin B group in a quantity of 1–2,000 μg; L-carnitine, creatine and choline in a quantity of 10,000–40,000 mg, and branched-chain amino acids in a quantity of 1–100 mg.

9. A composition according to claim 8, wherein the energy enhancer comprises at least one compound selected from the group consisting of vitamin B1, vitamin B2, niacinamide, vitamin B6, pantothenic acid, L-carnitine, creatine, choline chloride, leucine, isoleucine and valine.

10. A composition according to claim 1, wherein the antioxidant is selected from the group consisting of β-carotene in a quantity of 2 μg–200 mg, vitamin C in a quantity of 10–250 mg, vitamin E in a quantity of 8–30 I.U., and selenium in a quantity of 10–300 μg.

11. A composition according to claim 1, wherein the membrane stabilizer is selected from the group consisting of choline chloride, betaine chloride and methionine.

12. A composition according to claim 1, wherein the neuromuscular enhancer is octacosanol in quantities of 1–200 μg.

13. A liquid composition according to claim 1, containing per serving unit water at least the following components:

a) 1 to 35 g of at least one carbohydrate,
b) 2 to 2500 mg of at least one electrolyte,
c) 5 to 250 mg of at least one ammonia neutralizer,
d$_1$) 50–500 μg vitamins of the vitamin B group,
d$_2$) 50–500 mg L-carnitine, creatine and choline,
d$_3$) 5–50 mg of branched-chain amino acids,
e$_1$) 5–100 μg β-carotene,
e$_2$) 30–120 mg vitamin C,
e$_3$) 10–20 I.U. vitamin E,
e$_4$) 50–100 μg selenium,
f) 3 to 10 mg of at least one membrane stabilizer,
g) 3 to 100 μg of at least one neuromuscular function enhancer.

14. A liquid composition to be used as a rehydration drink, particularly suited for the administration to people who do heavy work under severe conditions at high temperatures, and to sports enthusiasts and athletes, containing per serving unit at least the following components:

| 20–100 g | Glucose Polymers |
|---|---|
| 10–150 mg | Maltodextrin |
| 1–15 g | Fructose |
| 100–2,500 mg | Potassium Bicarbonate |
| 20–60 mg | Sodium Bicarbonate |
| 100–2,000 mg | Potassium Chloride |
| 100–2,000 mg | Potassium Phosphate |
| 50–750 mg | Sodium Phosphate |
| 5–200 mg | Calcium Carbonate |
| 5–200 mg | Magnesium Carbonate |
| 10–750 g | D,L-Aspartic Acid (Magnesium Aspartate) |
| 20–750 μg | L-Arginine |
| 1–100 mg | Glutamate |
| 1–500 μg | Vitamin B1 |
| 10–2,000 μg | Vitamin B2 |
| 10–2,000 μg | Niacinamide |
| 10–2,000 μg | Vitamin B6 |
| 10–2,000 μg | Pantothenic Acid |
| 10–2,000 mg | L-Carnitine |
| 10–1,000 mg | Creatine |
| 4–40,000 mg | Choline (chloride) |
| 1–50 mg | Leucine |
| 1–100 mg | Isoleucine |
| 1–100 mg | Valine |
| 5–200 μg | β-Carotene |
| 20–250 mg | Vitamin C |
| 10–30 I.U. | Vitamin E |
| 10–300 μg | Selenium |
| 1–25 mg | Betaine (chloride) |
| 3–30 mg | Methionine |
| 1–200 μg | Octacosanol |

15. A liquid composition to be used as a rehydration drink, particularly suited for the administration to patients who exhibit dehydration symptoms due to severe diarrhea or vomiting, containing per serving unit at least the following components:

| 7–80 g | Glucose Polymers |
|---|---|
| 10–100 mg | Maltodextrin |
| 1–15 g | Fructose |
| 50–1,500 mg | Potassium Bicarbonate |
| 2–10 mg | Sodium Bicarbonate |
| 20–1,500 mg | Potassium Chloride |
| 20–1,500 mg | Potassium Phosphate |
| 5–75 mg | Sodium Phosphate |
| 5–200 mg | Calcium Carbonate |
| 5–200 mg | Magnesium Carbonate |
| 1–75 g | D,L-Aspartic Acid (Magnesium Aspartate) |
| 2–75 μg | L-Arginine |
| 1–50 mg | Glutamate |
| 1–500 μg | Vitamin B1 |
| 10–2,000 μg | Vitamin B2 |
| 10–2,000 μg | Niacinamide |
| 10–2,000 μg | Vitamin B6 |
| 10–2,000 μg | Pantothenic Acid |
| 1–200 mg | L-Carnitine |
| 5–100 mg | Creatine |
| 4–4000 mg | Choline (chloride) |
| 1–50 mg | Leucine |
| 1–100 mg | Isoleucine |
| 1–100 mg | Valine |
| 2–100 μg | β-Carotene |
| 10–90 mg | Vitamin C |
| 8–15 I.U. | Vitamin E |
| 10–200 μg | Selenium |
| 1–25 mg | Betaine (chloride) |
| 1–20 mg | Methionine |

| | |
|---|---|
| 1–20 µg | Octacosanol |

16. Process for the manufacture of a liquid composition to be used as a rehydration drink, wherein components a)–g) set forth in claim 1 are mixed, the resulting mixture being dissolved in a quantity of water at least sufficient to provide a solution wherein components a)–g) are substantially dissolved to provide a liquid composition ready for consumption by drinking.

17. Method of reducing one or more symptoms of dehydration of a human body by administration of a composition as claimed in claim 1.

18. A composition suited for preparing a rehydration drink by dissolving in water a liquid composition containing at least the following components:
   a) 1 to 100 g of at least one carbohydrate,
   b) 2 to 2500 mg of at least one electrolyte,
   c) 0.1 to 750 mg of at least one ammonia neutralizer,
   d) at least one energy enhancer,
   e) at least one antioxidant,
   f) 1 to 30 mg of at least one membrane stabilizer, and
   g) 1 to 200 µg of at least one neuromuscular function enhancer selected from the group consisting of choline and a higher saturated fatty alcohol, per serving unit of water.

19. A composition according to claim 1 containing 1 to 30 mg of at least one membrane stabilizer.

* * * * *